United States Patent [19]

Messing et al.

[11] 4,052,261
[45] Oct. 4, 1977

[54] PROCESS AND APPARATUS FOR THE FERMENTATION OF CARBOHYDRATE-CONTAINING NUTRIENT SUBSTRATE

[75] Inventors: Theodor Messing, Mulheim; Karl H. Wamser, Moers, both of Germany

[73] Assignee: Standard-Messo Duisburg Gesellschaft Fuer Chemietechnik mit Beschraenkter Haftung & Co., Duisburg, Germany

[21] Appl. No.: 726,778

[22] Filed: Sept. 27, 1976

[30] Foreign Application Priority Data

Sept. 27, 1975 Germany .............................. 2543307

[51] Int. Cl.$^2$ .......................... C12D 1/04; C12B 1/04
[52] U.S. Cl. ................................ 195/36 R; 195/109; 195/142
[58] Field of Search ...................... 195/36 R, 109, 126

[56] References Cited

U.S. PATENT DOCUMENTS 3,000,791  9/1961  Schweiger ........................ 195/36 R
3,846,245  11/1974  Kondis et al. ........................ 195/109

Primary Examiner—Lionel M. Shapiro
Attorney, Agent, or Firm—Bacon & Thomas

[57] ABSTRACT

A process and apparatus for the preparation of citric acid by fermentation of carbohydrate-containing nutrient substrates carried out in a fermentation chamber and having two separate air supply systems is disclosed wherein highly sterile air is preheated through coarse-fine-absolute filters, UV gate, and overheating to 120° C, and fed into the fermentation chamber during the germination phase of a fermentation of carbohydrate-containing nutrient substrate in a quantity sufficient to maintain the chamber at a slightly positive pressure; the fermentation chamber is heated separately and independently of the air supply during the germination phase; the feeding of the highly sterile air and the heating of the fermentation chamber are discontinued during the fermentation phase, and fresh, normally filtered, unconditioned air is introduced in a quantity sufficient to maintain the fermentation solution at an optimum fermentation temperature.

9 Claims, 1 Drawing Figure

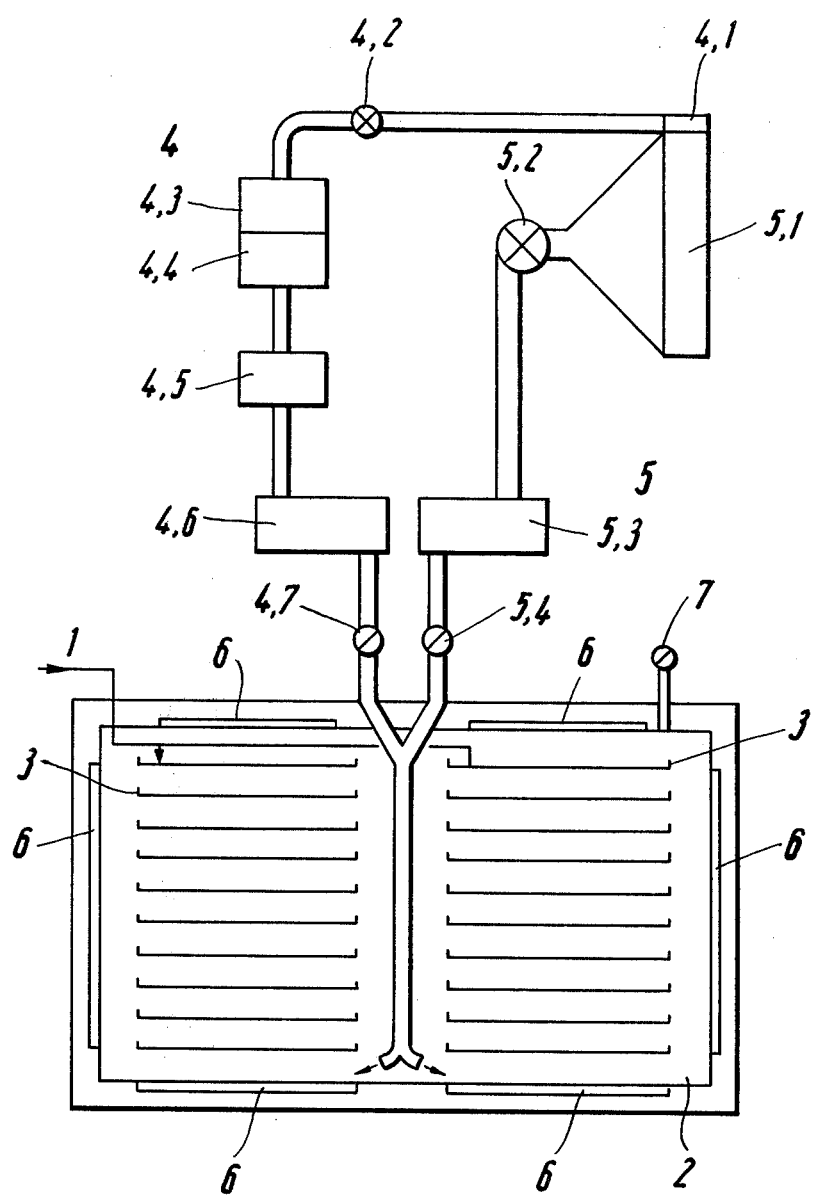

PROCESS AND APPARATUS FOR THE FERMENTATION OF CARBOHYDRATE-CONTAINING NUTRIENT SUBSTRATE

BACKGROUND OF THE INVENTION

1. Field of the Invention

The invention relates to a process and an apparatus for the fermentation of carbohydrate-containing nutrient substrates, particularly of molasses, in the preparation of citric acid. More particulaly, the invention relates to a process and apparatus for the inoculation of a fermentation solution with a fermentation agent in a sterile fermentation chamber, forming in a germination phase, a layer of the fermentation agent covering the entire surface of the fermentation solution, and then converting the sugar into citric acid, with the addition of air, in a fermentation phase.

2. Description of the Prior Art

Since the discovery of the citric acid forming capability of certain mould fungi; primarily aspergillus types, carbohydrate-containing nutrient substrates have been known to be suitable to undergo a fermentation process for the technical preparation of citric acid. Several substances such as sugar-containing products, starch, and starch-containing raw materials after sachharification are used as the nutrient substrate. Of these nutrient substrates, molasses has been an especially suitable substrate for fermentation. In the conventional processes, the liquid nutrient substrate which is to be fermented is first brought to a sugar content of 12 to 20 percent and is enriched with nutrient salts and possibly with fermentation-promoting additives. The enriched nutrient substrate is then sterilized, following the adjustment to the most favorable pH value. The sterilized fermentation substrate is fed from the cooker, through sterile lines, into flat pans, designated fermenting vessels, which are arranged on top of each other in the so-called fermenting room. Prior to filling, the vessels and the chambers must be sterilized with a disinfectant. All measures which are required for a sterile fermentation must be taken with special care because, otherwise, sensitive disorders through infections, penicillium types, yeasts, or bacteria are unavoidable. This fact represents a considerable disadvantage in the present practice of fermenting carbohydrate-containing nutrient substrates.

After the filling of the fermentation solution into the vessels, inoculation with spores of the micro-organism takes place. During the germination phase, usually about two days there is no heat development because citric acid is not yet generated during this time. A continuous mould cover is, however, formed during this period. It is widely recognized, therefore, that the vessels must be subjected to an external source of heat during germination. Without the supplemental addition of heat, the fermentation solution would be cooled, due to radiation, to the point that the temperature of the fermentation solution would be insufficient to support the germination. A small amount of oxygen is also required during this phase of the procedure.

Up to now, the loss of heat by radiation during the germination phase is compensated for by the introduction of large quantities of conditioned air, i.e., tempered and moistened, if required. Disadvantages of this technique arise from the required sterility of the blown-in air. This problem is further compounded by the large quantity of heated air which is necessary to prevent dropping of the temperature of the fermentation solution into ranges which prevent successful fermentation. Accordingly, the requirement of introducing these large quantities of air into the chambers without affecting the sterile environment can be fulfilled only with considerable effort. The requirement for a high degree of sterility is particularly important for the germination phase to prevent the reduction of yields, and in some cases, even total failure. Therefore, when employing such large quantities of air as heat carriers, it is not certain that infections would not also be carried into the chambers with the large quantity of air, especially in view of the size of the air conditioning system for the tempering and moistening, and the complexity of the associated filters.

After a good development of the mould cover during the germination phase, the citric acid formation starts and the so-called fermentation phase begins. It is characterized by the fact that, in the conversion of the sugar into citric acid, large quantities of heat are liberated, which must be removed from the chambers. The total process takes about 7 to 11 days. About 60 to 90 percent of the originally available sugar is converted into citric acid. The fermentation liquid is then drawn from the vessels and fed into vats in which the acid is precipitated as calcium citrate with the aid of milk of lime. The mould cover is washed and pressed and the wash water is combined with the concentrated citric acid solution in the precipitation vat. In accordance with the existing conventional processes, the heating air, required during the germination phase, as well as the cooling air, which takes care of the removal of the heat during the fermentation phase, are simply fed into the chambers through a single combined heating/cooling system.

In summary, this practice has been found to have a negative effect on the operating reliability of the overall process. Because the air which is fed into the chamber as heat carrier during the germination phase is used to maintain the temperature of the fermentation solution, and the quantities must therefore be correspondingly large, infections cannot be avoided, in spite of all efforts to assure the sterility of the air. The control of the fermentation solution temperature is carried out through a complicated control system with multiple variable dependent functions, in which both the quantities of air and also their temperatures and moistures are adjusted in accordance with the required fermentation climate.

The air, which is fed into the chamber during the germination phase, must be especially well filtered and even sterilized because of the increased susceptibility of the fermentation solution to infections; this means the application of considerable resources in view of the quantities of air which are used. In case of failure of one of the above-mentioned necessary conditions for carrying out the process, the result can be infections or undercooling of the fermenatation solution, which is associated with a poor fermentation yield or loss of a chamber.

SUMMARY OF THE INVENTION

Therefore, it is an object of the present invention to provide a process and an apparatus for the fermentation of carbohydrate-containing nutrient substrates, allowing a reliable and simplified implementation of the fermentation process.

It is also an object to provide a process and apparatus which reduce the resources which are used for filtering, sterilizing, and conditioning the air movement in connection with auxiliary heat supply and removal in the fermentation of carbohydrate-containing nutrient substrates.

It is further an object of the present invention to enable a considerable reduction in the susceptibility to contamination and infection during the germination phase.

These and other objects and advantages are achieved, in accordance with the present invention by a process carried out with an apparatus having a fermentation chamber and an air supply system, the process being characterized in that:

highly sterile air is preheated through coarse-fine-absolute filters, UV gate, and over-heating to 120° C, and fed into the fermentation chamber during the germination phase of a fermentation of carbohydrate-containing nutrient substrate in a quantity sufficient to maintain the chamber at a slightly positive pressure;

the fermentation chamber is heated separately and independently of the air supply during the germination phase;

the feeding of the highly sterile air and the heating of the fermentation chamber are discontinued during the fermentation phase, and fresh, normally filtered, unconditioned air is introduced in a quantity sufficient to maintain the fermentation solution at an optimum fermentation temperature.

Accordingly, it is one embodiment of the present invention to conduct the process with an apparatus having two air systems provided for one fermentation chamber. More particularly, the apparatus of the present invention provides one air system for the germination phase with highly sterile air and a second air system for the fermentation phase with fresh, unconditioned air, which is only filtered. Because the heating required during the fermentation phase is provided independently of the air system, the heating means can be configured in accordance with the specific properties of the particular system. The requirements of introducing only as much air into the fermentation chamber during the germination phase as needed maintained at a slight positive pressure is based on the principle that, during the germination phase, the oxygen requirement is low and therefore, little air need be introduced. For purposes of sterility, however, it is necessary to feed in a certain quantity of air so that the chamber is maintained with a slight positive pressure, thus preventing unfiltered air from penetrating into the chamber through leakage. In a preferred embodiment, air is introduced in a quantity sufficient to create and maintain a positive pressure in the chamber of between about 5 and about 50 mm water column. Accordingly, a high-grade sterilization system is required only for the quantity of air necessary to achieve this purpose. Thus, the sterilization system can be of a substantially reduced capacity in comparison with prior art systems; for example a system providing only about one percent of sterilized air formerly required, will be required under the present invention. It is also an advantage that an automatic adjustment system and a control system are not required for this purpose. Only a simple switching valve need be provided for the opening and closing of the air supply. Of course more than two air systems may comprise the air supply means in the apparatus of the present invention as long as the sterilized air supply system is separate and independent from the second air system which is more particularly described hereinafter.

In this manner, the conditions for the germination phase are fulfilled in an optimum manner. The chamber is kept warm by an independent heating means and it is kept under pressure through the supply of sterilized air in small quantity.

The operation of the process of the present invention is carried out, keeping in mind the following operational characteristics. During the course of a fermentation charge, the temperature of the fermentation solution first drops after filling and inoculation, and the development of heat at the beginning of the fermentation process then again heats the solution up, so that a typical curve pattern for the temperature of the fermentation solution develops. At the beginning of the fermentation phase, the temperature of the fermentation solution must be maintained at a certain favorable level through cooling. This is accomplished efficiently through the connection of a second air system, which is provided in accordance with this invention, after the first, above-described air system, the sterilized air system, is turned off. During the fermentation phase, fresh, normally filtered, unconditioned air is fed in for maintaining the temperature of the fermentation solution constant during the fermentation phase. The filtering of the air during the fermentation phase does not require nearly as critical a degree of perfection as is required for the germination phase because the fermentation solution is considerably less susceptible to contamination or infection during the fermentation phase. In one embodiment, a possibility for heating the air by way of conventional heating means is provided to assure against low temperatures during the fermentation phase, such as temperature which could perhaps occur in Winter. Conversely, in another embodiment, air which is too warm and saturated, for example in the tropics, can be further conditioned in a corresponding cooling step with conventional cooling means. Thus, the second air system may optionally contain heating or cooling means as called for by the particular operating environment of the process.

In summary, the present invention provides a considerable simplification of apparatus needed and an operationally reliable, economical process, giving a high output yield as the chief advantages.

While the positive pressure maintained in the fermentation chamber during the germination phase is preferably a positive pressure of about 5 mm to 50 mm water column, an even more preferable positive pressure of about 20 mm water column is desired. Described in a different manner, the actual amount of air suitable for introduction into the chamber during the germination phase in a preferred embodiment of the present invention may be as low as 1 cubic meter of air per hour per cubic meter of fermentation solution.

Under ideal circumstances, the fermentation phase of the process of the present invention is carried out at a constant temperature. More specifically, the introduction of air in sufficient quantities is adjusted so that the temperature of the fermentation solution is maintained constant. This enables the production of optimum yields of the final citric acid product. Accordingly, the air supplied to the fermentation chamber during the fermentation phase may be either heated or cooled depending on the prevailing temperatures by which the process is being carried out. In any case, it is within the concept of the present invention to adjust the temperature of the fermentation solution relative to the temperature of the environment during the fermentation phase.

The apparatus for implementing the process for the fermentation of carbohydrate-containing nutrient substrates, especially molasses in the preparation of citric acid is characterized, in accordance with the present invention, by a fermentation chamber, a heating means for the fermentation chamber, and two air supply means which are independent thereof. The air supply means are adapted for the germination phase on the one hand, and the fermentation phase on the other, whereby one air supply means or air system is designed for the feeding of small quantities of air which is sterilized in a sterilization apparatus, and the second air supply means or air system is designed as a cooling system to maintain a constant temperature in the fermentation solution. Appropriate configurations of the apparatus of the invention are more fully described hereinafter.

Further details, advantages, and characteristics of the invention result from the following description of a preferred embodiment and the associated drawing of which the only FIGURE.

FIG. 1, schematically shows a fermentation chamber of a citric acid production system.

A liquid carbohydrate-containing substance such as molasses is used as the starting material for the citric acid fermentation. The molasses is provided with fermentation-promoting additives and sterilized after the adjustment of the most favorable pH value. This sterilized fermentation solution reaches the fermentation chamber 2, through sterile conduits 1, wherein flat vessels 3 are arranged over each other for accepting the fermentation solution. The fermentation chamber 2 and the vessels 3 have been sterilized prior to filling.

Two air supply means or air systems 4 and 5, which are separate from each other, are connected to the fermentation chamber 2. Air system 4 is provided for the germination phase, and air system 5 is operative during the fermentation phase. In addition, fermentation chamber 2 is equipped with a wall heating unit or element 6. Through these measures, the strict separation of the germination and fermentation phases, which is essential for this invention, is made possible. Air system 4 for the germination phase consists of coarse filter 4.1, ventilator 4.2, fine filter 4.3, absolute filter 4.4, UV gate 4.5, air overheater 4.6 and valve 4.7, as well as the associated conduits. The wall heating unit 6 consists of conventional heating elements which are provided in walls, ceiling, and floor.

In addition, air system 5 for the fermentation phase is connected to the fermentation chamber 2, and consists of coarse filter 5.1, ventilator 5.2, absolute filter 5.3, and valve 5.4, as well as the associated conduits through which unconditioned, normally filtered air can be fed into the fermentation chamber 2.

For extreme temperature conditions, an apparatus must be so constructed, for example, in winter to preheat air which is too cold, or in tropical countries, to cool air which is too warm and to humid. This is carried out through a partial flow, which is not illustrated in the figure, which is installed between the coarse filter 5.1 and the absolute filter 5.3. The discharge of the air takes place through an air discharge valve 7.

Through the described air systems 5 and 4, as well as the separate wall heating unit 6, the processes of air supply and chamber heating are separated during the germination phase. The fermemtation chamber 2 is kept warm during the germination phase in that the walls, which cause the significant dissipation losses, are provided with heating elements, which compensate for the heat losses. In addition, an air supply with an extremely small quantity of air takes place during the germination phase, because the oxygen requirement during this phase is so low that the quantity of air which is in the chamber is basically sufficient. For reasons of maintaining sterile conditions, a slightly positive pressure is therefore produced with the sterile air which is fed in during the germination phase, thus avoiding the penetration of impure normal air through leakages of the fermentation chamber 2 during the germination phase. Depending on the size of the fermentation chamber 2, a quantity of air in the order of magnitude of 100 to 300 $m^3/h$ is introduced into the fermentation chamber 2 during the germination phase. This quantity of air is sterilized in air system 4 for the germination phase. The supply takes place through the opening of the open/closed valve 4.7 in a simple manner.

In this manner, the conditions for the germination phase for the optimum course of the germination process are fulfilled. The fermentation chamber 2 is kept sufficiently warm through the wall heating 6, and is kept with a slight positive pressure through the supply of the sterile air through the air system 4.

With the beginning of the development of heat, when the fermentation phase starts, the fermentation solution which is in the vessels 3 is heated by the exothermic processes. At a certain temperature in the fermentation solution, which indicates the end of the germination phase, and the beginning of the fermentation phase, air system 4 and the wall heating 6 are turned off and air system 5, which is configured as cooling air system, is turned on. For this purpose, valves 4.7 and 5.4 are switched over. Normally filtered air reaches the fermentation chamber 2 through air system 5. By known means, the temperature in the fermentation solution is automatically controlled during the fermentation phase, by means of the quantity of air which is blow in.

In this particular embodiment of the present invention and contrasted with prior art systems, in which, as initially described, a conditioning of the air was necessary, no conditioning or sterilization is carried out in air system 5 during the fermentation phase. The air is fed into fermentation chamber 2 unconditioned through filters 5.1 and 5.3. Of course, air system 5 can be equipped with heating or cooling means as an assurance against extremely low or extremely high temperatures, and thus saturated air temperatures, if necessary in special cases.

EXAMPLE

40 $m^3$ of molasses mash is prepared according to the prescription described in Bios Final Report No. 489, No. 22, p. 2, 3 further reported by Ullmann Encyclopadie der Technischen Chemie, 4. Aufl., Bd. 9, p. 626 – 629. The sterilized fermentation solution is then charged into the fermentation chamber of about 500 $m^3$ total volume of the apparatus as illustrated in FIG. 1, Air is then introduced into the air sterilization system 4 for the germination phase of the process and passes through coarse filter 4.1, ventilator 4.2, fine filter 4.3, absolute filter 4.4, UV gate 4.5, air overheater 4.6, valve 4.7 and into the fermentation chamber. The air flow into fermentation chamber through the sterile air supply system is maintained during the germination phase as a positive pressure of 20 mm. The quantity of air introduced into the fermentation chamber during the germination phase is up to 1 cubic meter/$m^3$ fermentation chamber volume · h. After a period of 16 – 48 hours, the temperature of the fermentation solution begins to increase and the sterile air supply through air system 4 is discontinued. The temperature of the fermentation solution is then allowed to increase to temperatures between 30° – 39° C and fresh, normally filtered, unconditioned air is simultaneously and continuously introduced into the fermentation chamber in such a way that the fermentation solution is maintained at temperatures between 30° –39° C for a period of 6 – 8 days. After approximately 7 – 9 days from the start, the fermentation is completed and citric acid is removed from the fermentation vessel by conventional techniques. The yield of citric acid according to this example is 75 – 85% from the initial molasses sugar.

What is claimed:

1. Process for the fermentation of carbohydrate-containing nutrient substrate in the preparation of citric acid, wherein a fermentation solution is inoculated with a fermentation agent in a fermentation chamber, a layer of the fermentation agent covering the entire surface of the nutrient substrate is formed in a germination phase, and subsequently a fermentation phase is carried out, characterized in that air is pretreated to a highly sterile state and fed into the fermentation chamber during the germination phase in a quantity sufficient to maintain the chamber at a slight positive pressure; the fermentation chamber is heated separately and independently of the air supply during the germination phase; the feeding of the highly sterile air and the heating of the fermentation chamber are discontinued during the fermentation phase, and fresh, normally filtered, unconditioned air is introduced in a quantity sufficient to maintain the fermentation solution at an optimum fermentation temperature.

2. The process according to claim 1 wherein the carbohydrate-containing nutrient substrate is molasses.

3. The process according to claim 2 wherein air is pretreated by passing through coarse-fine-absolute filters, UV gate, and being subjected to overheating to 120° C.

4. The process according to claim 1, characterized in that a positive pressure of 5 mm water column to 50 mm water column, is maintained in the fermentation chamber during the germination phase.

5. The process according to claim 4 wherein the positive pressure is about 20 mm.

6. The process according to claim 1, characterized in that the quantity of air introduced into the chamber during the germination phase is at least 1 $mm^3$ air/h/$m^3$ fermentation solution.

7. The process according to claim 1, characterized in that, during the fermentation phase, the fermentation chamber is heated to the extent of the heat losses of the fermentation chamber, independently of the air supply.

8. The process according to claim 1, characterized in that, during the fermentation phase, the quantity of air is sufficient to maintain the temperature of the fermentation solution.

9. The process according to claim 1, characterized in that, in the fermentation phase, the air is additionally heated or cooled in case of prevailing extreme surrounding temperatures.

* * * * *